(12) United States Patent
Burn et al.

(10) Patent No.: US 7,977,861 B2
(45) Date of Patent: Jul. 12, 2011

(54) BLENDED DENDRIMERS

(75) Inventors: Paul Leslie Burn, Oxford (GB); Ifor David William Samuel, Fife (GB)

(73) Assignees: Isis Innovation Limited, Oxford (GB); The University Court of the University of St. Andrews, Fife (GB)

( * ) Notice: Subject to any disclaimer, the term of this patent is extended or adjusted under 35 U.S.C. 154(b) by 864 days.

(21) Appl. No.: 10/525,616

(22) PCT Filed: Aug. 28, 2003

(86) PCT No.: PCT/GB03/03732
§ 371 (c)(1),
(2), (4) Date: Mar. 21, 2005

(87) PCT Pub. No.: WO2004/020504
PCT Pub. Date: Mar. 11, 2004

(65) Prior Publication Data
US 2005/0247911 A1  Nov. 10, 2005

(30) Foreign Application Priority Data
Aug. 29, 2002  (GB) .................................. 0220080.6

(51) Int. Cl.
*H01L 51/54* (2006.01)
*C09K 11/06* (2006.01)
(52) U.S. Cl. ... 313/504; 313/506; 257/40; 257/E51.028; 257/E51.042; 257/E51.043; 257/E51.044; 428/690; 428/917
(58) Field of Classification Search ........................ None
See application file for complete search history.

(56) References Cited

U.S. PATENT DOCUMENTS

| 4,871,779 | A | * | 10/1989 | Killat et al. ..................... 521/28 |
| 5,714,166 | A | * | 2/1998 | Tomalia et al. ............... 424/486 |
| 6,020,457 | A | | 2/2000 | Brothers et al. |
| 6,255,424 | B1 | | 7/2001 | Knauss |
| 2002/0102434 | A1 | * | 8/2002 | Inoue et al. .................. 428/690 |
| 2005/0079385 | A1 | * | 4/2005 | Nomura et al. ............... 428/690 |

FOREIGN PATENT DOCUMENTS

| EP | 893 482 | 1/1999 |
| JP | 2002/0207740 | 1/2002 |
| JP | 2002/080838 | 3/2002 |
| JP | 2002/121169 | 4/2002 |

(Continued)

OTHER PUBLICATIONS

Baldo et al., Physical Review B, (2000), vol. 62, No. 16, pp. 10,958-10,966.*

(Continued)

*Primary Examiner* — D. Lawrence Tarazano
*Assistant Examiner* — Brett A Crouse
(74) *Attorney, Agent, or Firm* — Quarles & Brady LLP

(57) ABSTRACT

A composition is described comprising a mixture of at least two different dendrimers A and B which possess the same core and the same repeating unit or units in the dendrons. Either the generation of at least one of said dendrons in one of said dendrimers (A) is different from the generation of at least one of the dendrons in the other of said dendrimers (B), or the number of dendrons in one of said dendrimers, or both, is different from the number of dendrons in the other of said dendrimers, or both.

20 Claims, 2 Drawing Sheets

Dendrimer A of generation n = 2

Dendrimer B of generation n + 1 = 3

FOREIGN PATENT DOCUMENTS

| | | |
|---|---|---|
| WO | WO 99/10362 | 3/1999 |
| WO | WO 99/21935 | 5/1999 |
| WO | WO 99/32540 | 7/1999 |
| WO | WO 01/59030 | 8/2001 |
| WO | WO 02/066552 | 8/2002 |
| WO | WO 02/066575 | 8/2002 |
| WO | WO 02/067343 | 8/2002 |

OTHER PUBLICATIONS

Mijovic et al., Macromolecules, (2007), vol. 40, pp. 5212-5221.*
Encyclopedia Britannica, Online, Copyright 2004, Conductivities.*
IUPAC Compendium of Chemical Technology, 2nd ed. (the "Gold Book"). McNaught et al., (http:goldbook.iupac.org).*
Hawley's Condensed Chemical Dictionary, 15th Edition, (2007), p. 929.*
Zeng et al., Dendrimers In Supramolecular Chemistry, 97 Chemical Rviews, ACS 1681-1712 (1997).
S. Lo et al., Green Phosphorescent Dendrimer For Light-Emitting Diodes, 13 Adv. Mater. 975-979 (2002).
J. Markham et al., High-Efficiency Green Phosphorescence From Spin-Coated Single-Layer Dendrimer Light-Emitting Diodes, 80 Appl. Phys. Lett. 2645-2647 (2002).
Pei-Wei Wang et al., Electroluminescent Diodes From a Single-Component Emitting Layer of Dendritic Macromolecules, 8 Adv. Mater. 237-241 (1996).
M. Halim et al., Conjugated Dendrimers For Light-Emitting Diodes: Effect of Generation, 11 Adv. Mater. 371-374 (1999).
A. Freeman et al., Dendrimer-Containing Light-Emitting Diodes: Toward Site-Isolation of Chromophores, 122 J. Am. Chem. Soc. 12385-12386 (2000).
A. Adronov et al., Light-Harvesting Dendrimers, Chem. Commun. 1701-1710 (2000).
C. Kwok et al., Synthesis and Light-Emitting Properties Of Difunctional Dendritic Distyrylstilbenes, 34 Macromolecules 6821-6830 (2001).
J. Lupton et al., Control Of Mobility In molecular Organic Semiconductors by Dendrimer Generation, 63 Physical Review B 155206-1-155206-8, (2001).
J. Lupton et al., Control Of Electrophosphorescence In Conjugated Dendrimer Light-Emitting Diodes, 11 Adv. Funct. Mater. 287-294 (2001).
Y. Luo et al., Fabrication Of Ag Nanoparticle-Encapsulating Multilayer Films Based on PAMAM Dendrimers With Covalent Interlayer Linkages 89 J. App. Polymer Science 1515-1519 (2003).
W. Zhao et al., Upconverted Emission From Pyrene and Di-tert-butylpyrene Using Ir(ppy)3 as Triplet Sensitizer, 110 J. Phys. Chem. 11440-11445 (2006).
H. Xin et al., Photoluminescence and Electroluminescence Of the Exciplex Formed Between a Terbium Ternary Complex and N,N'-diphenyl-N,N'-bis(3-methylphenyl)-1,1'-diphenyl-4,4'-diamine, 4 Phys. Chem. Phys. 5895-5898 (2002).

* cited by examiner

Dendrimer A of generation n = 2    Dendrimer B of generation n + 1 = 3

BLENDED DENDRIMERS

This application claims priority on GB0220080.6 filed on Aug. 29, 2002 and PCT/GB2003/003732 filed on Aug. 28, 2003.

This invention relates to blending of dendrimers, and to their use in opto-electronic devices, in particular light-emitting diodes.

BACKGROUND

Light-emitting devices based on organic light-emitting diodes (OLEDs), also known as organic electroluminescent (EL) devices, are an emerging display technology. In essence an OLED comprises a thin organic layer or stack of organic layers sandwiched between two electrodes, such that when a voltage is applied visible or other light is emitted. At least one of the electrodes must be transparent to light. For display applications the light must of course be visible to the eye, and therefore at least one of the electrodes must be transparent to visible light.

There are two principal techniques that can be used to deposit the organic layers in an OLED: thermal evaporation and solution processing. Solution processing has the potential to be the lower cost technique due to its potentially greater throughput and ability to handle large substrate sizes. Significant work has been undertaken to develop appropriate materials, particularly polymers. More recently dendrimers that are photoluminescent in the solid state have been shown to have great promise as solution processable light-emitting materials in OLEDs (S-C. Lo, et al *Adv. Mater.*, 2002, 13, 975; J. P. J., Markham, et al *Appl. Phys. Lett.*, 2002, 80, 2645).

Dendrimers are branched macromolecules with a core and attached dendrons. Dendrons are branched structures comprising branching units and optionally linking units. The generation of a dendron is defined by the number of sets of branching points; see FIG. 1. Dendrons with the same structure (architecture) but a higher generation, or order, are composed of the same structural units (branching and linking units) but have an additional level of branching. There can be surface groups on the periphery of the dendrons.

Light-emitting dendrimers typically have a luminescent core and in many cases at least partially conjugated dendrons. Further examples of light-emitting dendrimers include those found in P. W. Wang, et al *Adv. Mater.*, 1996, 8, 237; M. Halim, et al *Adv. Mater.*, 1999, 11, 371; A. W. Freeman, et al J. Am. Chem. Soc., 2000, 122, 12385; A. Adronov, et al *Chem. Comm.*, 2000, 1701.; C. C. Kwok, et al *Macromolecules*, 2001, 34, 6821. Light-emitting dendrimers have the advantage over light-emitting polymers in that the light-emitting properties and the processing properties can be independently optimised as the nature of the core, dendrons and surface groups can be independently altered. For example, with dendrimers that contain light-emitting cores, the emission colour of a dendrimer can be changed by simply changing the core. The nature and generation of the dendrons in a dendrimer have been shown to influence the charge transporting and processing properties (J. M. Lupton, et al *Phys. Rev. B*, 2001, 63, 5206). Other physical properties, such as viscosity, may also make dendrimers more easily tailored to the available manufacturing processes than polymers.

Dendrimers have previously been used in OLED applications as a single component in a film (i.e. a neat film) or in a mixture with a molecular material (Markham et al, loc cit) or in a mixture of more than one dendrimer of different type (i.e. different cores), e.g. J. M. Lupton et al. *Adv. Funct. Mater.*, 2001, 11, 287. In this later case one type of organic dendrimer was used as a host for a guest organometallic dendrimer but the efficiency of the device was low.

Although progress has been made in the development of solution processible OLEDs there is still the need for OLEDs with improved efficiency and lifetime.

The current invention is directed to the production of mixed dendrimer films and OLEDs containing them that solve some of the problems in the prior art.

SUMMARY OF THE INVENTION

According to the present invention there is provided a composition, preferably in the solid state, comprising a mixture of at least two different dendrimers A and B which possess the same core and the same repeating unit or units in the dendrons wherein either the generation of at least one of said dendrons of one of said dendrimers (A) is different from the generation of at least one of the dendrons in the other of said dendrimers (B), or the number of dendrons in one of said dendrimers is different from the number of dendrons in the other of said dendrimers, or both the number of dendrons and the generation of at least one of the dendrons in one said dendrimer (A) is different from the number and generation of dendrons in the other said dendrimer (B).

Thus in one embodiment, the composition comprises a mixture of at least one dendrimer A of generation n, where $n \geq 1$, and a second dendrimer B of generation n+x, where x=1, 2 or 3, where the two dendrimers have the same core and surface groups as each other and the dendrons of the two dendrimers have the same structure but the dendrons of dendrimer B have more branching points than dendrimer A, such that dendrimer B is of higher generation. In a preferred form of this embodiment, the number of dendrons in dendrimer A is the same as in dendrimer B. By way of illustration, FIG. 1 shows a schematic of dendrimer A, which is depicted as a second-generation dendrimer, compared with a higher-order (third) generation dendrimer B.

The mixture of dendrimers, and indeed the composition, is preferably in the solid state or is otherwise stable against (net) interchange between dendrimers (A) and (B). Thus, the mixture is preferably one in which the relative amounts of dendrimers (A) and (B) are substantially constant over time. It may well be the case that a process intended to produce a single type of dendrimer, and whose end product is indeed a single type of dendrimer, will generate as a transient intermediate state a mixture of dendrimers of different generation as growth proceeds. In such mixtures, however, the relative amounts of the various species present will vary over time. The mixture of the present invention, at least in preferred embodiments, is different from such a transient state in that it is stable since the conditions are such that the lower generation dendrimer cannot grow into the higher generation form, or vice-versa or the number of dendrons within the dendrimer cannot change. The reason for this will usually be because the mixture is in the solid state. Alternatively when the mixture is in solution the solvent and any other components in the solution will, under the chosen conditions, be un-reactive with the dendrimers so that the relative proportion of the dendrimers in the mixture does not change i.e. any other ingredients present in the mixture will be unreactive. Thus, in a preferred method of production, the dendrimers are produced separately from one another and are mixed in the solid state or under other conditions that prevent undesired change, such as being dissolved in an inert solvent.

For most purposes it is expected that the present mixture and composition will be in the form of a solid film. Thus, according to the second aspect of the present invention there is provided a solid film of a composition comprising the dendrimer mixture of the invention.

According to the third aspect of the invention there is provided an OLED device comprising, in sequence, layers of: an optional substrate, an electrode, a first optional charge-transporting layer, an emissive layer, a second optional charge-transporting layer and a counter electrode, wherein one of the emissive layer, the first or second charge-transporting layers, if present, especially the emissive layer, is a film according to the current invention. Thus, in its simplest form, the device may consist of the emissive layer between electrodes.

Usually one charge-transporting layer, if present, will be a hole-transporting layer while the other optional charge-transporting layer will be an electron-transporting layer. In general, each charge-transporting layer may comprise two or ore layers which may be the same as, or different from, each other.

In one embodiment the film comprising a mixture of dendrimer A and dendrimer B also contains one or more additional species, such as light-emitting dopants, charge-transporting species and/or additional molecular, dendritic and/or polymeric materials. The molecular species may possess the same group as the core of the dendrimer but without the dendrons attached and may or may not have other substituents attached. The dendritic materials can be similar to dendrimers A or B.

DETAILED DESCRIPTION OF THE INVENTION

Figure 1:
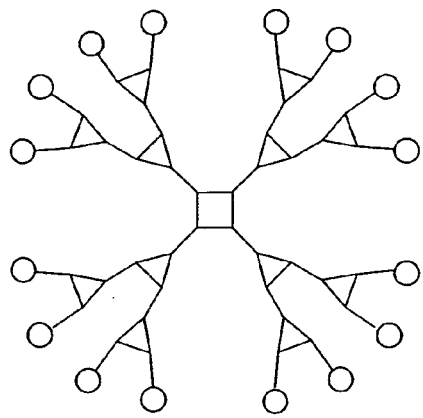
FIG. 1 shows a schematic view of dendrimer A, which is depicted as a second-generation dendrimer, and compared with the higher order (third) generation dendrimer B.
Figure 1:
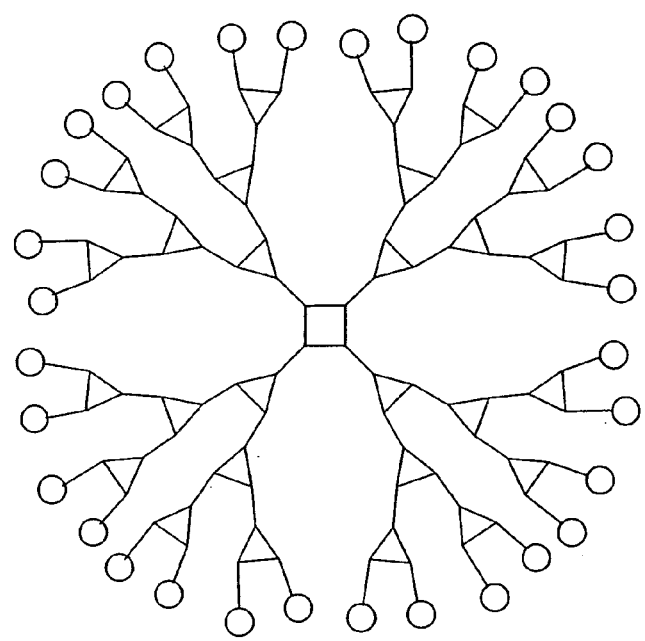

This invention is directed towards the use of mixtures of dendrimers of different generations, but otherwise of the same structural type, i.e. having the same core, and the same dendron structural units. The type and/or number of surface groups of the different dendrimers can be different providing they give solubility in the same solvent. However, it is preferred that the nature and number of surface groups attached to each distal group on the different dendrimers are the same.

Unexpectedly, it has been found that it is possible to mix visible light-emitting dendrimers of different generations such that the quantum efficiency of a device with a solid film of the mixture is higher than that if the film were comprised of only the lower generation dendrimer or only of the higher generation dendrimer. The combination of dendrimers of different generations has been found to allow solid films of improved quality, e.g. more uniform characteristics, particularly thickness, to be formed compared with films formed from the lower generation dendrimer. A further unpredicted result is that mixing of different generation dendrimers permits control of the level of charge mobility within the mixture, which, when such a mixture is used as a solid electroluminescent film in an OLED device, in turn affects the device characteristics as a whole.

With the mixture of dendrimers A and B, preferably the dendrimer B is one generation higher than dendrimer A, i.e. x=1 (or at least one dendron is one generation higher than a dendron of the other dendrimer). In one embodiment dendrimer A is first generation, i.e. n=1 and dendrimer B is second generation, i.e. x=1. In an alternative embodiment, dendrimer A is at least second generation. When three or more dendrimers are mixed at least one is preferably of higher generation than at least one of the others.

Dendrons with the same structure (architecture) but a higher generation, or order, are composed of the same structural units (branching and linking units) but have an additional level of branching, i.e. an additional repetition of these branching and linking units.

The mixture of dendrimers may optionally contain an additional molecular and/or dendrimeric and/or polymeric material. For example the mixture may contain a light-emitting dopant and/or a charge transporting species. A preferred combination is for the two light-emitting dendrimers to be mixed with a charge transporting species.

Although the present invention covers mixtures of dendrimers of differing generation in general, dendrimers that have at least one inherently at least partially conjugated dendron are preferred in OLED applications. In this context an inherently at least partially conjugated dendron means a dendron that has conjugation between the branching groups and linking units (if present) of the dendron, but because of the arrangement of the branching points the pi-system is not necessarily fully delocalised. Such dendrons can also be termed conjugated dendrons. In a preferred embodiment the said dendrimers (A and B) are capable of emitting light particularly of the visible spectrum. Particular dendrimers of interest are organometallic dendrimers, i.e. metal-containing dendrimers with a metal ion incorporated as part of the core. In an alternative embodiment the dendrimers have charge-transporting properties.

Figure 2:
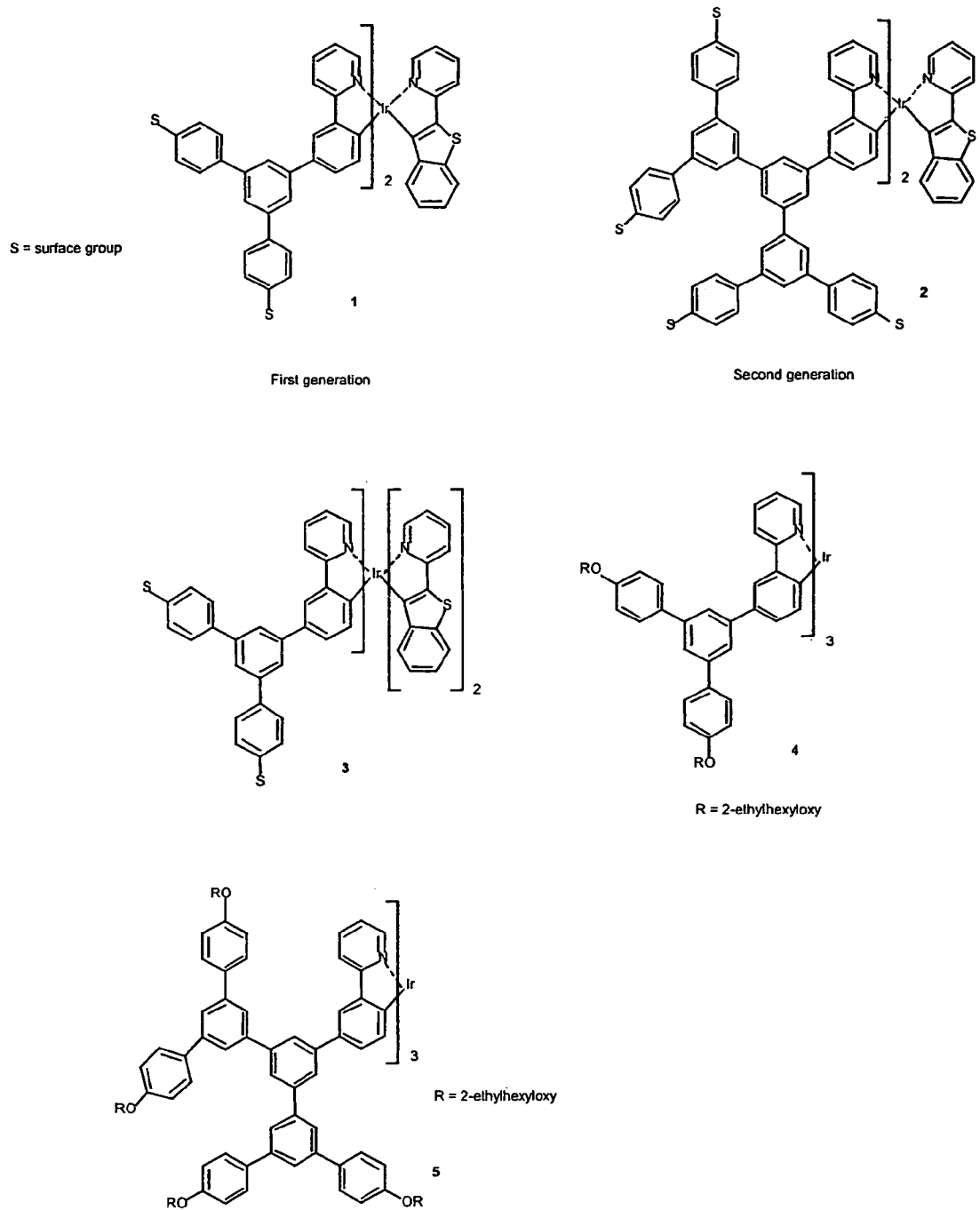
FIG. 2 shows red emitting iridium dendrimers.

Since the dendrimers have the same core, it may be the case that they each have the same number of dendrons attached to the core, e.g. in FIG. 1 they both have 4 dendrons attached to the core. Preferably all of the dendrons in dendrimer B will be of higher generation than the dendrons in dendrimer A but this is not essential. At least one, though, must be of a different generation. In the case of organometallic dendrimers in addition to the ligands with dendrons attached, there may be non-dendritic ligands that form part of the core and these will of course not change as the generation of the dendrimer changes. For example, FIG. 2 shows red emitting iridium dendrimers with two dendritic ligands and one non-dendritic ligand, for both generations i.e. 1 and 2. In an alternative embodiment there is a mixture of dendrimers that contain the same basic emissive chromophore but differ in the number of dendrons (although the dendrons contain the same branching and optionally linking units and surface groups, e.g., 1 and 3).

All the usual surface groups, such as those discussed in WO 99/21935, to which reference should be made, can be used. These include further-reactable alkene, (meth)acrylate, sulphur-containing, or silicon-containing group; sulphonyl group; polyether group; $C_1$- to -$C_{15}$ alkyl group; amine group; mono-, di- or tri- $C_1$- to -$C_{15}$ alkyl amine group; —COOR group wherein R is hydrogen or $C_1$- to -$C_{15}$ alkyl; —OR group wherein R is hydrogen, aryl, or $C_1$- to -$C_{15}$ alkyl or alkenyl; —$O_2$SR group wherein R is $C_1$- to -$C_{15}$ alkyl or alkenyl; —SR group wherein R is aryl, or $C_1$- to -$C_{15}$ alkyl or alkenyl; —$SiR_3$ group wherein the R groups are the same or different and are hydrogen, $C_1$- to -$C_{15}$ alkyl or alkenyl, or —SR' group (R' is aryl or $C_1$- to -$C_{15}$ alkyl or alkenyl), aryl, or heteroaryl. In general the surface groups of the dendrimers A and B in the mixture will be the same.

In one embodiment the surface groups are chosen such that the dendrimer can be patterned. For example, a crosslinkable group can be chosen as a surface group, which can be crosslinked, e.g. upon irradiation or by chemical reaction. Alternatively, the surface groups can comprise protecting groups that can be removed to leave crosslinkable groups. In general, the surface groups are selected so that the dendrimer mixture is soluble in solvents suitable for solution processing, e.g. THF, toluene, chloroform, chlorobenzene, xylenes and alcoholic solvents such as methanol. Alternatively, the type and/or number of surface groups attached to each distal group is different in the dendrimers, providing they give solubility in the same solvent to the dendrimers (and providing the dendrons and core are of the same structure). In the preferred embodiment the dendrimers also have the same surface groups. Where t-butyl groups are the surface groups attached to phenyl rings it is preferable that more than one is attached to each of the distal phenyl units.

A variety of different types of dendrimer can be used in the mixtures. As indicated above dendrimers which have at least one inherently partially conjugated dendron are preferred such as those described in WO99/21935 having the formula (I):

CORE-[DENDRITE]$_n$ (I)

in which CORE represents an atom or group, n represents an integer of at least 1 and DENDRITE, which may be the same or different if n is greater than 1, represents an inherently at least partly conjugated dendritic molecular structure comprising aryl and/or heteroaryl groups and alkenyl groups connected to each other via a carbon atom of an alkenyl group to a ring carbon atom of an aryl or heteroaryl group, CORE terminating in the first single bond which is connected to a ring carbon atom of an (hetero)aryl group to which more than one at least partly conjugated dendritic chain is attached, said ring carbon atom forming part of DENDRITE, the CORE and/or DENDRITE being luminescent including ones where the dendrons are not all the same as disclosed in PCT/GB02/00765 in general those having the formula (II):

CORE-[DENDRITE$^1$]$_n$[DENDRITE$^2$]$_m$ (II)

in which CORE represents an atom or group, n and m, which may be the same or different, each represent an integer of at least 1, each DENDRITE$^1$, which may be the same or different when n is greater than 1, and each DENDRITE$^2$, which may be the same or different when m is greater than 1, represent dendritic structures, at least one of said structures being fully conjugated and comprising aryl and/or heteroaryl groups and, optionally, vinyl and/or acetylenyl groups, connected via sp$^2$ or sp hybridized carbon atoms of said (hetero) aryl, vinyl and acetylenyl groups, and at least one branching point and/or link between the branching points in DENDRITE$^1$ being different from those in DENDRITE$^2$, CORE terminating in the single bond which is connected to a sp$^2$ hybridized (ring) carbon atom of the first (hetero)aryl group to which more than one conjugated dendritic branch is attached, said ring carbon atom forming part of said fully conjugated DENDRITE$^1$ or DENDRITE$^2$ and CORE terminating at the single bond to the first branching point for the other of said DENDRITE$^1$ or DENDRITE$^2$, at least one of the CORE, DENDRITE$^1$ and DENDRITE$^2$ being luminescent, and those of formula (III):

CORE-[DENDRITE]$_n$ (III)

in which CORE represents an atom or group, n represents an integer of at least 1, each DENDRITE, which may be the same or different, represents an inherently at least partially conjugated dendritic molecular structure which comprises aryl and/or heteroaryl and, optionally, vinyl and/or acetylenyl groups, connected via Sp$^2$ or sp hybridized carbon atoms of said (hetero) aryl, vinyl and acetylenyl groups, and wherein the links between adjacent branching points in said DENDRITE are not all the same, CORE terminating in the single bond which is connected to a Sp$^2$ hybridized (ring) carbon atom of the first (hetero)aryl group to which more than one dendritic branch is attached, said ring carbon atom forming part of said DENDRITE, the CORE and/or DENDRITE being luminescent, ones where the dendrons comprise aryl-aryl ligands as disclosed in PCT/GB02/00739, in general those having the formula: (IV)

CORE-[DENDRITE(-Q$_a$)]$_n$ (IV)

in which the CORE represents an atom or group, n represents an integer of at least 1, Q is a proton or a surface group such that at least one Q is a surface group, a is an integer and DENDRITE, which may be the same or different if n is greater than 1, represents a conjugated dendritic structure comprising aryl and/or heteroaryl groups connected to each other via bonds between sp$^2$ hybridised ring atoms of said aryl or heteroaryl groups, CORE terminating in the first single bond which is connected to an sp$^2$ hybridised ring atom of an (hetero)aryl group to which more than one conjugated dendritic branch is attached, said atom forming part of the DENDRITE, the CORE and/or DENDRITE being luminescent, as well as organometallic dendrimers as disclosed in PCT/GB01/00750 typically those having the formula (V):

CORE-[DENDRITE]$_n$ (V)

in which CORE represents a metal ion or a group containing a metal ion, n represents an integer of 1 or more, each DENDRITE, which may be the same or different, represents an inherently at least partially conjugated dendritic molecular structure comprising aryl and/or heteroaryl groups or nitrogen and, optionally, vinyl or acetylenyl groups connected via sp$^2$ or sp hybridised carbon atoms of said (hetero)aryl vinyl and acetylenyl groups or via single bonds between N and (hetero)aryl groups, CORE terminating in the single bond which is connected to an sp$^2$ hybridised (ring) carbon atom of the first (hetero)aryl group or nitrogen to which more than one at least partially conjugated dendritic branch is attached, said ring carbon atom or N forming part of said DENDRITE, and nitrogen-core containing dendrimers as disclosed in WO01/59030 in general those having the formula (VI):

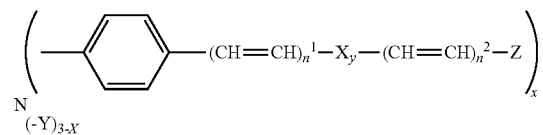

where x is 3, 2 or 1, n$^1$ and n$^2$, which may be the same or different, are 0 or 1 to 3, X represents a divalent mono- or poly-aromatic and/or heteroaromatic moiety, the or each Y, which may be the same or different if x is 1, represents hydrogen or an optionally substituted hydrocarbon group, Z represents an inherently at least partly conjugated dendritic molecular structure comprising aromatic and/or heteroaromatic groups and optionally, alkenylene groups, connected to each other either via a carbon atom of an heteroaromatic group to a ring carbon atom of another (hetero)aromatic group or, if an alkenylene group is present via a ring carbon atom of an (hetero)aromatic group to a carbon atom of an alkenylene group, said dendritic molecular structure being connected to the remainder of the molecule via a ring carbon atom of an (hetero) aromatic group to which more than one at least partly conjugated dendritic chain is attached, one or more of the (hetero) aromatic rings of the dendrimer optionally being substituted, Z and/or the remainder of the molecule, excluding any groups Y, being luminescent, typically x must be 3, to which reference should be made for further details.

In an asymmetric dendrimer of a given generation having the formula (II) at least one link and or branching point in DENDRITE1 is different to that in DENDRITE2. In a higher generation of the same type of asymmetric dendrimer the links and branching points in DENDRITE1 will be the same as in DENDRITE1 in the lower generation and the links and branching points in DENDRITE2 will be the same as in DENDRITE2 in the lower generation, and either DENDRITE1 or DENDRITE2 or both in the higher generation dendrimer will have more branching and optionally linking units than in the lower generation dendrimer. It will be appreciated, however, that in a dendrimer of formula (II) only one of DENDRITE1 and DENDRITE2 need be of different generation.

The present invention is particularly directed towards the mixing of differing generation organometallic dendrimers of the type covered by PCT/GB02/00750 in which a metal-ion is part of the core. In such dendrimers, with chromophores comprising metal-ion complexes incorporated as part of the core, i.e. the metal cation is part of the core, the dendrons separate the core chromophores of adjacent molecules. These have been shown to work well in electroluminescent devices due to the reduced tendency towards concentration quenching and triplet-triplet annihilation. The preferred organometallic dendrimers contain the ions iridium (which is particularly preferred), platinum, rhodium or rhenium (which is at present least preferred) as part of the core. Less preferred are organometallic dendrimers where the dendrons quench the luminescence of the core, in particular platinum porphyrin cored dendrimers with stilbene dendrons attached to the meso-positions. It is also preferred that the organometallic dendrimers do not require counteranions associated with them to balance the charge. It is therefore preferred that, in the organometallic dendrimers, the combination of ligands attached to the co-ordination sphere of the metal cation will lead to a neutral dendrimer. It is also preferred that the dendron be connected to a ligand which is at least in part attached to the metal ion via a metal-carbon bond. It is further preferred that the metal carbon bond be part of a cyclometallated ring. It is also preferred that there be dendrons attached to two or more ligands of at least one of the dendrimers of the mixture. Preferred organometallic dendrimers include those derived from a core with at least one ligand with a nitrogen-containing heteroaryl, for example pyridine, pyrimidinyl, pyrazinyl, pyridazinyl, imidazolyl, quinolinyl, isoquinolinyl attached to a (hetero)aryl where aryl can be a fused system, for example substituted or unsubstituted phenyl or benzothiophene, naphthyl, anthryl, phenanthryl, benzamidazolyl, carbazolyl, fluorenyl, pyrazolinyl, oxazolinyl, oxadiazolinyl, triazolyl, triazinyl, thiadiazolyl, benzimidazolyl, benzoxazolyl, furyl, and more specifically 2-phenylpyridine, which is preferred, 2-thienylpyridine, benzo(h)quinoline, 2-phenylbenzoxazole, 2-phenylbenzothiazole, 2-pyridyltrianaphthalene and iminobenzene in the case of iridium, around the central metal with aryl-aryl dendrons. Fluorescent dendrimers that show a propensity to pi-stack and give excimer emission can have the film packing disrupted by mixing different generations, thus improving colour purity. This different packing also gives control of charge mobility in charge transport layers.

In Example 18 of our PCT/GB02/00750 we describe the preparation of a dendrimer corresponding to compound 1 in FIG. 2 where s=2-ethylhexyloxy. This is obtained by reacting 2-benzo[b]thiophene-2-ylpyridine with a dichloro-Iridium complex with two phenyl pyridine ligands each being mono-substituted by the specified dendron. It is believed that the resulting complex is a mixture of a compound with a single phenyl pyridyl ligand along with the desired compound with two phenyl pyridyl ligands i.e. the product is a mixture of compound 1 with compound 3. Such a mixture is less preferred. It is preferred to obtain the mixture by mixing homogeneous (i.e. individual compounds) together.

The molar ratio of the dendrimers A and B forming the mixture may favour the higher-generation or the lower-generation dendrimer within the mole range of 1:1 to 1:50, for example 1:1 to 1:5. It is also possible to mix dendrimers with the same core, dendrons and, optionally, surface groups of three or more different generations.

The properties of dendrimers make them ideal for solution processing. Preferred dendrimers can be dissolved in a solvent, the solution deposited onto a substrate, and the solvent removed to leave a solid film. Conventional solution-processing techniques can be used, for example spin coating, printing (e.g. inkjet) and dip coating. The resulting solid film containing the mix of dendrimers A and B forms another aspect of the current invention. The solid film can be either fluorescent or phosphorescent. The solid film is preferably formed on one side of a substrate; the thickness of the solid film is preferably no greater than 2 microns.

The present aspect of the invention also provides an OLED incorporating a solid film of this invention. In its simplest form, an organic light-emitting or electroluminescent device can be formed from a light-emitting layer sandwiched between two electrodes, at least one of which is transparent to the emitted light. More commonly there is at least one hole-transporting layer between the anode and the light-emitting layer and/or at least one electron-transporting layer between the light-emitting layer and the cathode. In one preferred embodiment the said film comprising the dendrimer mixture forms the light-emitting layer in an OLED. It is particularly preferred that the dendrimers are the light-emitting species in this light-emitting layer or, at least, are the principal light-emitting species. In an alternative embodiment, the film comprising the dendrimer mixture forms a charge-transporting layer in an OLED. For example a first generation charge-transporting dendrimer such as 4,4',4"-tris[3,6-{4-[2-ethylhexyloxy]phenyl}-N-carbazolyl]triphenylamine, could be mixed with higher generations of this type of dendrimer. Suitable light-emitting dopants that could be mixed with such charge-transporting dendrimers include phosphorescent organometallic molecular materials such as fac-tris(phenylpyridine) iridium and related compounds designed to give different colours, and organometallic dendrimers.

Such a device can have a conventional arrangement comprising a transparent substrate layer, e.g. a glass or PET layer, a transparent electrode layer, a light-emitting layer and a back electrode. The anode, which is generally transparent, is preferably made from indium tin oxide (ITO) although other similar materials including indium oxide/tin oxide, tin oxide/antimony, zinc oxide/aluminium, gold and platinum can also be used, as can conducting polymers such as PANI (polyaniline) or PEDOT/PSS. The cathode is normally made of a low work function metal or alloy such as Al, Ca, Mg, Li or MgAl or optionally with an additional layer of LiF. In an alternative configuration, the substrate may be made of an opaque material such as silicon and light is emitted through the opposing electrode. The OLED devices may be actively or passively addressed.

For a typical OLED device, as described above where the dendrimer mixture is emissive, a solution of the dendrimer mixture can be applied over a transparent electrode layer, the solvent evaporated and then subsequent charge-transporting layers can be applied. The thickness of the dendrimer mixture layer in the OLED is typically 10 nm to 1000 nm, preferably no more than 200 nm, more preferably 30 nm to 120 nm. When a hole transport layer is incorporated between the anode and the emissive dendrimer mixture layer the hole transport material must not be removed to a significant extent during the solution deposition.

An OLED device incorporating an emissive layer comprising the dendrimer mixture may optionally have an adjacent first and/or second charge-transporting layer. When the dendrimer mixture is a phosphorescent emitter, it has been found that it is particularly beneficial to have a hole-blocking/electron-transporting layer between the light-emitting dendrimer mixture layer and the cathode. Suitable materials for such a hole-blocking/electron-transporting layer are known and include 2,9-dimethyl-4,7-diphenyl-1,10-phenanthroline (BCP), 1,3,5-tris[2-N-phenylbenzimidazolyl)benzene (TPBI), aluminium tris(8-hydroxyquinolate) (Alq), aluminium bis(2-methyl-8-quinolato)-4-phenylphenolate (BAlq) and 2-biphenyl-5(4'-t-butylphenyl)oxadiazole (PBD).

Furthermore, additional emissive (fluorescent or phosphorescent) or charge-transporting species may optionally be added to the mixture of dendrimers A and B to improve device characteristics, e.g. efficiency and lifetime. It may further be of benefit to include one or more other molecular and/or dendrimeric and/or polymeric species in the mixture of dendrimers to give improved performance. Hence it is preferred that the molecular, dendritic or polymeric species can transmit charge in its own right, and that it is therefore for example a conjugated polymer or dendrimer. In one embodiment such additional components form a part of the total composition from 95 and 5 mol %. For example, with compositions that contain phosphorescent organometallic dendrimers, additional charge-transporting components include TPBI, PBD, BCP, 4,4'-bis(N-carbazole)bipbenyl (CBP), 4,4',4"-tris(N-carbazolyl)triphenylamine (TCTA), and tris-4-(N-3-methylphenyl N-phenyl) phenylamine (MTDATA).

Such mixtures of dendrimers can also be used in other device applications such as photovoltaic cells which can contain one or more layers. When used in photovoltaic cells, the dendrimers in the dendrimer mixture must in general be capable of absorbing light and/or transporting charge. The composition may be used as a homogeneous layer in a photovoltaic device or mixed with other molecular and/or dendritic and/or polymeric materials. The mixed dendrimers may be used in one or more layers of the photovoltaic device. In photovoltaic applications the organometallic dendrimers within the mixture need not necessarily be neutral.

The Examples that follow further illustrate the present invention.

EXAMPLE 1

A green-emitting multilayer device comprising as follows: ITO/CBP:(G1:G2, 1:2), 80:20 wt %/BCP 60 nm/LiF 1.2 nm/Al 100 nm. Here first (G1) and second generation (G2) (see FIGS. 2, 4 and 5) iridium dendrimers were mixed in a mole ratio of 1:2 and in turn mixed with a (bipolar) charge-transporting material CBP in a weight ratio of 20:80. In addition to this emissive layer, a 60 nm layer of a hole-blocking material BCP is incorporated between the emissive layer and the cathode. This device gave a maximum power efficiency of 35-39 cd/A and quantum efficiency of 20-25 lm/W at 4-6V giving brightnesses of 2-40 cd/m$^2$. The maximum observed brightness was 4000 cd/m$^2$ at 12V. The turn-on voltage was 4.2V.

COMPARATIVE EXAMPLE

In comparison, for the device configuration ITO/G1 4:CBP/BCP/LiF/Al we found that the average maximum power efficiency was 8 lm/W (17 cd/A) at brightnesses around 1065 cd/m$^2$ and voltages of 7.5 V. The turn on voltages were between 3.5 V and 4.2 V and peak brightnesses reached 16000 cd/M$^2$ at 12V. The weight ratio of G1:CBP in this device was 20:80 wt %. In the device configuration TO/G2 5:CBP/BCP (60 nm)/LiF (1.2 nm)/Al (100 nm) we found that the efficiency as 23 cd/A at a brightness of 30 cd/m$^2$ and a voltage of 6V. The peak brightness as 1000 cd/m$^2$ at 10V, and the turn on voltage was 4.4V. The ratio of G2:CBP in this device was 46:54 wt %.

As can be seen from these results, the efficiency of the OLED device containing both G1 and G2 is higher than the efficiency of either the device containing just G1, or the device containing just G2.

The results given above were obtained from devices that were prepared according to the following procedure. The ITO substrates were etched by photolithography and treated under O$_2$ plasma for 10-20 mins. Films of CBP doped with a dendrimer mixture (or a single dendrimer for comparison purposes) were deposited by spin-coating from chloroform using a concentration of around 5 mg/ml onto ITO. The dendrimer: CBP solutions were prepared and films spun in a glove-box environment (<1 ppm O$_2$/H$_2$O). Typically this produced films with the thickness in the region of 30-60 nm depending upon spin speed selected. The devices were then completed by sequential evaporation of BCP (40-90 nm), LiF (1.2-1.5 nm), and Al (100 nm) under typical base pressures of 2×10$^{-7}$ mBar.

The invention claimed is:

1. A composition comprising a mixture of at least two different dendrimers A and B which possess the same core and the same repeating unit or units in the dendrons wherein either the generation of at least one of said dendrons in one of said dendrimers (A) is different from the generation of at least one of the dendrons in the other of said dendrimers (B), or the number of dendrons in one of said dendrimers is different from the number of dendrons in the other of said dendrimers, or both the number of dendrons and the generation of at least one of the dendrons in one said dendrimer (A) is different from the number and generation of dendrons in the other said dendrimer (B), and wherein (i) the dendrimers A and B are phosphorescent organometallic dendrimers which have at least one inherently at least partially conjugated dendron, and (ii) the composition is charge transporting and/or emissive.

2. A composition according to claim 1 wherein the generation of the, or at least one of the, dendrons, in one of said dendrimers is 1.

3. A composition according to claim 1 wherein the generation of the, or at least one of the, dendrons in one of said dendrimers is one greater than that of the, or at least one of the, dendrons in the other said dendrimer.

4. A composition according to claim 1 wherein the generation of the, or all the, dendrons in one of said dendrimers is one greater than that of the other said dendrimers.

5. A composition according to claim 1 wherein the molar ratio of one said dendrimer to the other dendrimer is from 1:1 to 1:50.

6. A composition according to claim 1 which comprises dendrimers of three different generations where the dendrimers are comprised of the same core, and dendron type and surface groups.

7. A composition according to claim 1 wherein the at least one dendron which is of different generation in A and B is inherently at least partially conjugated.

8. A composition according to claim 1 wherein at least one of said dendrimers A and B has two inherently at least partially conjugated dendrons.

9. A composition according to claim 1 wherein at least one of said dendrimers A and B has three inherently at least partially conjugated dendrons.

10. A composition according to claim 1 wherein all dendrons of said dendrimers A and B are inherently at least partially conjugated dendrons.

11. A composition according to claim 1 wherein the said dendrimers have the same surface groups.

12. An organic light emitting device comprising, in sequence, layers of: an optional substrate, an electrode, a first optional charge-transporting layer, a light emissive layer, a second optional charge-transporting layer and a counter electrode, wherein at least one of the emissive layer, first optional charge-transporting layer and second optional charge-transporting layer is a solid film comprising a composition as claimed in claim 1 which is capable of emitting visible light.

13. A device according to claim 12 which has at least one charge-transporting layer.

14. A device according to claim 12 wherein the emissive layer also contains an emissive dopant, as additional component.

15. A device according to claim 12 wherein the emissive layer also contains one or more charge-transporting species, as additional component.

16. A device according to claim 12 wherein the emissive layer also contains a molecular species, as additional component.

17. A device according to claim 12 wherein the emissive layer also contains a dendritic species, as additional component.

18. A device according to claim 12 wherein the emissive layer also contains a polymer, as additional component.

19. A device according to claim 14 wherein the additional component comprises 95 to 5 mol % of the total composition.

20. A photovoltaic device that comprises at least a composition as claimed in claim 1.

* * * * *